(12) United States Patent
Koenig et al.

(10) Patent No.: US 7,196,022 B2
(45) Date of Patent: Mar. 27, 2007

(54) PRODUCTS FOR CONTROLLING MICROBIAL GENERATED ODORS

(75) Inventors: David William Koenig, Menasha, WI (US); Franklin M. C. Chen, Appleton, WI (US); Melanie A. Keomany, Oshkosh, WI (US); Jason Robert Borski, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 913 days.

(21) Appl. No.: 10/029,322

(22) Filed: Dec. 20, 2001

(65) Prior Publication Data

US 2003/0119396 A1 Jun. 26, 2003

(51) Int. Cl.
*B32B 27/12* (2006.01)
(52) U.S. Cl. .................. 442/123; 428/313.5; 422/5; 422/28
(58) Field of Classification Search ............ 442/123; 428/313.5; 422/5, 28
See application file for complete search history.

(56) References Cited

U.S. PATENT DOCUMENTS

| | | | |
|---|---|---|---|
| 3,964,486 A | 6/1976 | Blaney | |
| 5,861,145 A | 1/1999 | Lucas et al. | |
| 5,879,666 A | 3/1999 | Lucas et al. | |
| 6,191,010 B1 | 2/2001 | Falster | |
| 6,217,889 B1 * | 4/2001 | Lorenzi et al. | 424/401 |
| 6,229,062 B1 | 5/2001 | Mandell et al. | |

FOREIGN PATENT DOCUMENTS

| | | |
|---|---|---|
| EP | 103804 | 3/1984 |
| EP | 922452 | 6/1999 |
| EP | 922457 | 6/1999 |
| WO | WO 97/11220 | 3/1997 |
| WO | 97/31092 * | 8/1997 |
| WO | WO 97/32612 | 9/1997 |
| WO | WO 98/13021 | 4/1998 |
| WO | WO 98/56341 | 12/1998 |
| WO | WO 99/26619 | 6/1999 |
| WO | WO 99/47141 | 9/1999 |
| WO | WO 99/59538 | 11/1999 |
| WO | WO 00/00148 | 1/2000 |
| WO | WO 00/00226 | 1/2000 |
| WO | WO 00/00228 | 1/2000 |
| WO | WO 00/00232 | 1/2000 |
| WO | WO 00/57843 | 10/2000 |
| WO | WO 00/62730 | 10/2000 |
| WO | WO 00/62826 | 10/2000 |
| WO | WO 00/63486 | 10/2000 |
| WO | WO 00/63487 | 10/2000 |
| WO | WO 00/66187 | 11/2000 |
| WO | WO 01/28338 | 4/2001 |
| WO | WO 01/28339 | 4/2001 |
| WO | WO 01/45613 | 6/2001 |
| WO | WO 01/45615 | 6/2001 |
| WO | WO 01/47455 | 7/2001 |

OTHER PUBLICATIONS

PCT International Search Report for International Application No. PCT/US 02/34950dated Mar. 21, 2003.
Brzostek, et al., "Osmoregulation-dependent Expression of *Yersinia enterocolitica* Virulence Factors" Acta Microbiological Polonica, 1999, 48(1):31-37.
Caldas, et al., "Thermoprotection by glycine betaine and choline" Microbiology, 1999, 145:2543-2548.
Chambers, et al., "Inhibitors of bacterial growth in urine: what is the role of betaines?" International Journal of Antimicrobial Agnets, 1999, 11:293-296.
Peddie, et al., Osmoprotective activity, urea protection, and accumultion of hydrophillic betaines in *Escherichia coli* and *Staphylococcus aureus* Antonie van Leeuwenhoek, 1999, 75:183-189.
Peddie, et al., "Osmoprotective properties and accumulation of betaine analogues by *Staphylococcus aureus*" FEMS Microbiology Letters, 1998, 160:25-30.
Rudulier, et al., Molecular Biology of Osmoregulation, Science, 1984, 224:1064-1068.

\* cited by examiner

*Primary Examiner*—Elizabeth M. Cole
(74) *Attorney, Agent, or Firm*—Senniger Powers

(57) ABSTRACT

Absorbent products and wet wipes are disclosed that are useful in reducing the amount of ammonia produced by bacteria on or near the skin or in bodily fluids such as urine. The products described herein contain an osmoregulation protector which when introduced into a bacteria-containing environment interacts with the bacteria and reduces the amount of ammonia produced by the bacteria without significantly affecting the growth rate of the bacteria. The osmoregulation protectors described herein are particularly useful in combination with adult incontinence garments where the control of odors from bacterial by-products such as ammonia is highly desirable.

28 Claims, No Drawings

PRODUCTS FOR CONTROLLING MICROBIAL GENERATED ODORS

BACKGROUND OF THE INVENTION

The present invention relates to products which reduce the amount of ammonia produced by bacteria on or near the skin, or in bodily fluids such as urine. More specifically, the present invention relates to absorbent products and wet wipes which incorporate an osmoregulation protector which can interact with bacteria in urine and on or near the skin's surface and minimize the amount of ammonia produced by the bacteria. The osmoregulation protectors described herein are particularly useful in adult incontinence garments where the control of unwanted odors, such as the odor of ammonia, is highly desirable.

Human urine has a high level of osmotic strength and toxicity toward bacteria. Based on these characteristics, it could be assumed that bacterial growth in urine would be significantly inhibited such that foul odors, such as odors from ammonia, generated by the bacteria through metabolism would not be problematic. However, numerous bacteria have evolved the ability to adapt to high osmolarity and toxicity conditions by activating osmoregulation protectors such as betaine porters and accumulating organic osmolytes intracellularly. In other words, bacteria are able to avoid dehydration by taking up or synthesizing molecules that act as osmotic balancing agents such that large amount of salts cannot enter the bacterial membrane and dehydrate the cell. Transporters, such as betaine porters, move molecules or ions across the cellular membranes of bacteria by specifically binding and physically moving the substrate from one side of the membrane to the other. Both passive and active transport can be impacted by the betaine porters; that is, the porters can move substrates down a concentration gradient (no energy required) or they can move substrates against a concentration gradient (requires energy) to balance the water content of the cell.

Glycine betaine is a common osmoregulation protector used by bacteria in the presence of urine. Glycine betaine, while acting as an osmoregulation protector, does not significantly disrupt other normal cellular functions. Further, in some circumstances, glycine betaine will act to stabilize macromolecular structures to counteract the destabilizing effects of urea and keep the bacterial cell from tearing open. Because glycine betaine is commonly found in urine, the growth of bacteria in urine is common. Along with glycine betaine naturally synthesized by the bacteria, the presence of glycine betaine in voided urine promotes the rapid growth of bacteria by balancing osmotic forces and stabilizing the bacteria against the toxicity of urea and allowing for the subsequent increase of pH. In a cyclical pathway, ammonia is used as a nutritional substrate by the organisms, resulting in growth of more organisms and production of more ammonia, increasing the pH and lowering the osmotic pressure by decreasing the urea concentration. The pathway generates more and more ammonia as the bacteria continue to grow.

The production of ammonia by bacteria in urine can lead to the release of unwanted and offensive odors. The problem is particularly acute in the area of adult incontinence garments where odor control is highly desirable. Regardless of whether an absorbent product can control or all together stop leakage of urine upon release by a wearer, if the product cannot also control or eliminate the odor generated by the urine, or more precisely by the bacteria in the urine, the product is undesirable. As such, a need exists in the industry for absorbent products, such as adult incontinence products, that can control odors such as ammonia generated by bacteria contained in human urine.

SUMMARY OF THE INVENTION

The present invention relates to absorbent articles, such as adult incontinence garments, and wet wipes which are capable of reducing the amount of odorous compounds such as ammonia produced by bacteria contained in urine as well as bacteria held on or next to the skin's surface. Specifically, the absorbent articles and wet wipes described herein contain an osmoregulation protector which, when the product or wipe is used, contacts the urine and bacteria on or near the skin and suppresses the production of odorous compounds such as ammonia by the bacteria. This suppression of the production of odorous compounds such as ammonia occurs without significantly disrupting other bacterial cellular functions which could lead to the death of the bacterial cell. Further, the osmoregulation protectors described herein act to stabilize bacterial structures to counteract the destabilizing effects of urea.

Briefly, therefore, the present invention is directed to an absorbent product for minimizing the amount of ammonia produced by bacteria. The product comprises an osmoregulation protector which is capable of interacting with bacteria such that the production of ammonia by the bacteria is minimized.

The invention is further directed to an adult incontinence garment for minimizing the amount of ammonia produced by bacteria contained in urine voided by a wearer. The garment comprises an osmoregulation protector which is capable of interacting with the bacteria contained in the urine such that the production of ammonia by the bacteria is minimized.

The invention is further directed to a wet wipe for minimizing the amount of ammonia produced by bacteria. The wet wipe comprises a solution which contains an osmoregulation protector which is capable of interacting with bacteria on or near the skin's surface such that the production of ammonia by the bacteria is minimized.

Other objects and features of this invention will be in part apparent and in part pointed out hereinafter.

DETAILED DESCRIPTION OF THE PREFERRED EMBODIMENTS

In accordance with the present invention, it has been discovered that the production of ammonia and other odorous products by bacteria on or near the skin's surface or in a bodily fluid such as urine can be significantly reduced by introducing an osmoregulation protector into an absorbent product worn next to the skin or into a wet wipe used to clean skin after soiling. This discovery is particularly useful in the area of absorbent products used for incontinence garments where odors such as ammonia stemming from urination are particularly undesirable. Surprisingly, the introduction of an osmoregulation protector such as glycine betaine in a sufficient amount into the absorbent product results in a significant decrease in the production of ammonia by the bacteria when the absorbent product contacts voided urine. This decrease in ammonia production can result in a significant decrease in foul odors stemming from voided urine.

In accordance with the present invention, an osmoregulation protector is introduced into or onto an absorbent product or into the liquid phase of a wet wipe in an amount sufficient to minimize or substantially eliminate the production of ammonia or other odorous products by bacteria when the osmoregulation protector interacts with the bacteria. Although primarily discussed herein with respect to ammonia, it is intended that the other odorous products produced by bacteria and other microbes such as sulfur-containing compounds and fatty acids are to be included. The bacteria may be contained on or near the skin and in human waste products such as urine, feces, and menses. The osmoregulation protectors incorporated into the products described herein are particularly useful in urine-containing environments wherein the production of odorous ammonia is particularly acute. As used herein, the term "osmoregulation protector" means a compound which, by balancing osmotic forces between the interior of the cell and the exterior of the cell, aids in the survival of bacteria in a highly osmotic environment such as urine. The osmoregulation protectors described herein can be incorporated into or onto numerous products in accordance with the present invention such as, for example, diapers, training pants, adult incontinence garments, feminine napkins, tampons, interlabial pads, wound management products, bath tissue, facial tissue, diaper pails, liners for diaper pails, paper towels, refuse containers, bed pads, puppy pads, and other pet supply products. When these products, which contain the osmoregulation protector, are contacted or insulted by urine or another bacteria-containing liquid, the osmoregulation protector dissolves into the urine or other liquid, interacts with the bacteria, and effectively minimizes or substantially eliminates the production of ammonia by the bacteria such that the degree of foul odor released is reduced.

The osmoregulation protectors described herein can also be incorporated into the liquid phase of a wet wipe which could be, for example, used to clean urine or other bodily fluids from the skin after insult. When an osmoregulation protector is incorporated into the liquid phase of a wet wipe and contacted with urine or another bacteria-containing liquid, the osmoregulation protector migrates into the urine or other liquid, interacts with the bacteria, and effectively minimizes or substantially eliminates the production of ammonia by the bacteria such that the degree of foul odor released is reduced.

The products of the present invention incorporating an osmoregulation protector are highly useful in reducing the amount of ammonia produced by numerous types of bacteria contained in urine and other bodily fluids or wastes. Specifically, the products of the present invention incorporating the osmoregulation protectors are particularly effective in reducing the amount of ammonia produced from facultative bacteria. Examples of facultative bacteria which can produce ammonia at or near the skin's surface or in a liquid such as urine include, but are not limited to, for example, *Escherichia, Klebsiella, Enterobacter, Serratia, Citrobacter, Corynebacterium, Propionibacterium, Neisseria, Pseudomonas, Vibrio, Shigellae, Salmonella, Proteus*, and *Moraxella*. The products of the present invention reduce the amount of ammonia produced by all of these types of bacteria, as well as others.

A particularly useful and surprising property of the osmoregulation protectors described herein and incorporated into the products of the present invention is that the osmoregulation protectors, while significantly minimizing or eliminating the production of ammonia by bacteria in urine, for example, do not significantly disrupt or alter other cellular functions of the bacterial cell; that is, the osmoregulation protectors do not result in the death of the cell or decrease the growth rate of the cell. This is significant in that there is an advantage in simply minimizing or eliminating the ammonia produced by bacteria and in not limiting the growth of or killing the bacteria present on and near the skin, mucosa, or within the body (e.g., if the products of the present invention are tampons). The killing of bacteria is typically non-selective; that is all bacteria are killed whether the bacteria are beneficial or non-beneficial to the host organism. In the case of vaginal bacteria, for example, the reduced growth or killing of the bacteria in a specific area can be a serious problem as numerous bacterial species are required to maintain a healthy vaginal environment and balance the pH of the vagina. With the osmoregulation protectors and products of the present invention, only a very small amount, if any, bacteria are actually killed or their growth rate decreased as the osmoregulation protectors simply interact with the bacteria to reduce the amount of ammonia produced. Because the osmoregulation protectors are naturally occurring in some bodily fluids, and are naturally produced by bacteria, their presence in and around bacteria does not substantially alter other normal bacterial cell functions.

Any compound which acts as an osmoregulation protector in the presence of bacteria in urine, menses, or feces, for example, can be utilized with the products described herein to minimize the production of ammonia by the bacteria through the interaction of additional amounts of osmoregulation protectors, supplied via the product, with the bacteria in the fluid. Further, the osmoregulation protectors described herein can be used alone or in combination with other odor control technologies known in the art such as, for example, zeolite, cyclodextrin and/or disodium EDTA. Specifically, osmoregulation protectors such as glycine betaine, proline betaine, trigonelline, carnitine and arsenobetaine are preferred osmoregulation protectors for incorporation into the products of the present invention and, while substantially minimizing the production of ammonia by the bacteria, will not result in cell death or a significant decrease in cell growth. A particularly preferred osmoregulation protector is glycine betaine which is particularly effective in suppressing the production of ammonia by bacteria in the presence of urine.

Without being bound to a particular theory, it appears that the osmoregulation protectors, when introduced into the products of the present invention in a sufficient amount, interact with the bacteria present in urine (i.e., when the absorbent product is insulted and the osmoregulation protector is solubilized into the urine or other bodily fluid), for example, and interfere with the cellular membrane structure in such a way that the production of ammonia by the bacteria is substantially reduced. It appears that the introduction of an amount of osmoregulation protectors in addition to what is naturally present in urine and naturally synthesized by the bacteria, unexpectedly results in the bacteria not being capable of producing a significant amount of ammonia as compared to ammonia production in the absence of an additional amount of osmoregulation protectors. The interference and reduction occurs despite the fact that osmoregulation protectors such as glycine betaine are present in urine as voided by humans and also made in vitro by the bacteria themselves. It is believed that the interaction between the additional amount of osmoregulation protectors and the bacteria may occur in a number of ways independently, or may occur in a number of related ways. First, the interaction between the additional amounts of osmoregulation protectors and the bacteria may significantly alter the proton motive force of the bacterial membrane which in turn alters the bacterial membrane properties in such a way that active and/or passive transport of molecules through the bacterial membrane is inhibited, which directly affects the energy production of the bacteria. The interaction may also work in connection with a second interaction between the osmoregulation protectors of the products described herein and the bacteria wherein the transport of urease across the bacterial membrane is interrupted which could result in the upstream interference with urease production leading to a decreased ammonia production.

In accordance with the present invention, the osmoregulation protectors are introduced into or onto the absorbent products of the present invention in an amount sufficient to reduce the amount of ammonia produced by bacteria when the absorbent article is insulted with a liquid such as urine or menses and the osmoregulation protector interacts with the bacteria; that is, a sufficient amount of osmoregulation protectors are introduced into or onto the absorbent article such that when the article is insulted and the osmoregulation protectors contact the insulting liquid, there is an introduction of an additional amount of osmoregulation protectors into the insult as compared to the amount that is naturally occurring. This additional amount of osmoregulation protectors decreases the amount of ammonia produced by bacteria. In typical embodiments, from about 0.001 milligrams/gram of absorbent product to about 2 milligrams/gram of absorbent product, preferably from about 0.01 milligram/gram of absorbent product to about 2 milligrams/gram of absorbent product, and most preferably from about 0.1 gram/milligram of absorbent product to about 2 milligrams/gram of absorbent product of osmoregulation protector is sufficient to provide the additional amount of osmoregulation protector to realize the intended benefit of the products described herein. Although the introduction of amounts larger than the amounts specified herein of osmoregulation protectors into the absorbent articles are within the scope of the present invention, such amounts are not typically required for the benefits of the present invention to be realized and would generally only increase the ultimate cost of the product without significantly increasing its performance.

A significant and unexpected aspect of the products of the present invention which contain the additional amount of osmoregulation protectors is that, despite the naturally occurring presence of osmoregulation protectors in urine and the fact the bacteria in the presence of urine themselves synthesize osmoregulation protectants, the introduction of an additional amount of osmoregulation protectors above that which naturally occurs into the bacterial environment significantly reduces the amount of ammonia produced by the bacteria. This is surprising as bacteria rely on the same osmoregulation protectants to maintain and balance the osmotic forces on both sides of the cellular membranes in highly osmotic liquids such as urine. Without this balance, the bacteria could not live. Because the osmoregulation protectors are not toxic to the bacteria as the environment the bacteria live in contains the osmoregulation protectors, such protectors can reduce the amount of ammonia produced while not having a toxic effect on the bacteria.

The osmoregulation protectors described herein may be introduced directly into or onto an absorbent product, or may first be encapsulated into a shell material which releases the osmoregulation protector when wetted during use. The encapsulated shell is constructed of a material such that it will release the osmoregulation protectors upon wetting. The wetting of the encapsulated shell may cause the shell material to solubilize, disperse, swell, disintegrate, or may be permeable such that it disintegrates or discharges the osmoregulation protectors upon wetting. Suitable nanoencapsulation or microencapsulation shell materials include cellulose-based polymeric materials (e.g., ethyl cellulose), gelatin, carbohydrate-based materials (e.g., starches and sugars) and materials derived therefrom (e.g., dextrins and cyclodextrins) as well as other materials compatible with human tissues. The microencapsulation shell thickness may vary depending upon application, and is generally manufactured to allow the encapsulated protectors to be covered by a thin layer of encapsulation material, which may be a monolayer or thicker laminate layer, or may be a composite layer. The microencapsulation layer should be thick enough to resist cracking or breaking of the shell during handling or shipping of the product or during wear which would result in breakage of the encapsulation material and a premature release of the osmoregulation protectors. The microencapsulation layer should also be constructed such that humidity from atmospheric conditions during storage, shipment, or wear will resist a breakdown of the microencapsulation layer that would result in a premature release of the osmoregulation protectors.

Microencapsulated osmoregulation protectors should be located or be of a size such that the wearer cannot feel the encapsulated shell against the skin. Typically, the size of the microencapsulated shell should be no greater than about 25 micrometers. Although larger microencapsulated shell sizes may be utilized, they may result in a "gritty" or "scratchy" feeling on the skin of the wearer of the product.

The osmoregulation protectors described herein may be incorporated directly into numerous products to control the production of ammonia by bacteria present in human waste products such as urine and on or near the skin's surface. Specifically, the osmoregulation protectors can be incorporated into cellulosic materials, non-woven materials, and superabsorbent materials such that, upon insult, the osmoregulation protectors interact with the bacteria and reduce the amount of ammonia produced by the bacteria.

Typically, the osmoregulation protectors are not simply introduced onto or into a product without a stabilizing mechanism to ensure that the protectors remain in the desired area of the product. The osmoregulation protectors can be introduced onto a product utilizing various methods including, for example, spray coating, slot coating, printing, particle impingement, or a combination thereof. In spray coating, the osmoregulation protectors are thoroughly mixed with a substantially urine-soluble or urine-dispersable adhesive agent to disperse the osmoregulation protectors throughout the adhesive material. The adhesive material can comprise a urine-soluble adhesive which will partially or completely dissolve upon wetting with urine or other liquids and allow release of the osmoregulation protectors, or may be comprised of a material which disperses upon contact with urine allowing release of the protectors. Suitable adhesives include, for example, polyvinyl pyrrolidone and poylvinyl alcohol, and combinations thereof. After the adhesive and osmoregulation protectors are mixed, they can be applied by, for example, spraying, knifing, or roller coating, onto the desired area of the product and allowed to dry prior to packaging. It will be recognized by one skilled in the art that the protectors described herein can be distributed throughout the entire product, or can simply be introduced onto a particular area of a product depending upon the intended use of the product.

Similar to spray coating, the osmoregulation protectors may be introduced into or onto the products of the present invention through slot coating. In slot coating, an adhesive-osmoregulation protector as described above is introduced directly onto the desired area of the pad in "slots," discrete row patterns, or other patterns. Upon wetting, the adhesive allows a release of the osmoregulation protectors. Slot coating may be advantageous in certain applications wherein it is not desirable to coat the entire surface with an adhesive. In some circumstances, an adhesive coating over an entire surface may retard quick absorption of urine or other exudates into an absorbent core. When slot coating is utilized, channels are created where no adhesive is present and exudates may drain quickly. Slot coating may also be advantageous in certain applications where precise control of the location of the osmoregulation protectors is desired. Generally, slot coating rows are evenly spaced across the surface upon which they are applied, but may be spaced in specific patterns with varying spacing if desired.

In an alternative embodiment, the osmoregulation protectors can also be introduced onto or into a gas permeable liner, absorbent core, or another layer of a product in accordance with the present invention through the use of a vacuum driving force or through the use of a pressure differential. When utilizing a vacuum force, the osmoregulation protectors are positioned on the liner, absorbent core, or another layer while a vacuum driving force is applied to the opposite side of the liner, absorbent core, or another layer to drive the protectors into the fabric matrix of the liner, core or other layer. Varying degrees of vacuum can be applied depending upon the required depth of the protectors. In this embodiment, no adhesive is required. Once in the fabric matrix of the product, the protectors are stable until wetted. Alternatively, electrostatic forces or other means may be utilized to stabilize the osmoregulation protectors on the surface of the product.

In an alternative embodiment of the present invention, the osmoregulation protectors can be incorporated in various products in accordance with the present invention by incorporating the protectors into a liposome carrier or emulsion and introducing the liposome carrier or emulsion into or onto the product in the desired amount. This type of delivery system for the osmoregulation protectors allows for incorporation of the active material into fibers as well as nonwoven materials such as tissues, and into the solutions used in combination with wet wipes. Liposome carrier or emulsion systems may also be useable to incorporate the osmoregulation protectors into other products such as wound management products, feminine care products, bath tissue, adult incontinence garments, and/or deodorants.

In another embodiment of the present invention, the osmoregulation protectors described herein can be incorporated into a liquid cleansing solution useful, for example, with a fibrous wet wipe substrate. Typically the cleansing solution comprising the osmoregulation protectors will have a pH of from about 2 to about 9, more preferably from about 4 to about 7, and still more preferably from about 5 to about 6. Although the osmoregulation protectors described herein are active over a wide range of pH values, the above-referenced ranges provide optimum performance.

The osmoregulation protectors described herein can be incorporated into a cleansing cloth, pre-moistened wipe, wet wipe, udder wipe, hand wipe, face wipe, cosmetic wipe, household wipe, hospital wipe, industrial wipe and the like having the improved ability to control the amount of ammonia produced by bacteria. Materials suitable for the substrate of the wet wipe are well known to those skilled in the art, and are typically made from a fibrous sheet material which may be either woven or nonwoven. For example, the wet wipes incorporating the osmoregulation protectors of the present invention may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, wet wipes define a basis weight of from about 25 to about 120 grams per square meter and desirably from about 40 to about 90 grams per square meter.

In a particular embodiment, the wet wipes incorporating the osmoregulation protectors of the present invention comprise a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers.

The relative percentages of the polymeric microfibers and cellulosic fibers in the coform basesheet can vary over a wide range depending upon the desired characteristics of the wet wipes. For example, the coform basesheet may comprise from about 20 to about 100 weight percent, desirably from about 20 to about 60 weight percent, and more desirably from about 30 to about 40 weight percent of the polymeric microfibers based on the dry weight of the coform basesheet being used to provide the wet wipes.

Alternatively, the wet wipes incorporating the osmoregulation protectors of the present invention can comprise a composite which includes multiple layers of materials. For example, the wet wipes may include a three-layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film.

As previously mentioned, the wet wipes contain a cleansing formulation which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping. In a particular aspect, wherein the wet wipes are made from a coform material comprising from about 30 to about 40 weight percent polymeric microfibers based on the dry weight of the wipe, the amount of solution contained within the wet wipe is from about 300 to about 400 weight percent and desirably about 330 weight percent based on the dry weight of the wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container holding the wet wipes.

The solutions incorporating the osmoregulation protectors described herein which can be incorporated into wet wipes may also optionally contain a variety of other components which may assist in providing the desired wiping and cleaning properties. For example, additional components may include water, emollients, surfactants, preservatives, chelating agents, pH buffers, fragrances, antimicrobial actives, acids, alcohols, or combinations or mixtures thereof. The solution may also contain lotions and/or medicaments to deliver any number of cosmetic and/or drug ingredients to improve performance. To provide reduced skin irritation, the solution desirably includes at least about 80 weight percent water and more desirably at least about 90 percent water based on the total weight of the solution.

Typically, the solutions containing the osmoregulation protectors described herein used in combination with the wet wipe substrate comprise from about 0.001 milligram/milliliter of solution to about 2 milligrams/milliliter of solution, preferably from about 0.01 milligram/milliliter of solution to about 2 milligrams/milliliter of solution and most preferably from about 0.1 milligram/milliliter to about 2 milligrams/milliliter of solution of osmoregulation protector.

The present invention is illustrated by the following example which is merely for the purpose of illustration and is not to be regarded as limiting the scope of the invention or manner in which it may be practiced.

EXAMPLE 1

In this Example, various amounts of glycine betaine were introduced into a urine culture containing facultatively grown Proteus mirabilis bacteria to determine whether the glycine betaine affected the production of ammonia by the bacteria in the urine culture. Also, the pH of each sample was measured at various points to determine whether ammonia was being neutralized in the sample.

Proteus mirabilis (ATCC 29906) bacteria were recovered from frozen state by growing the appropriate bacterial coated MicroBank Bead (Pro Lab, Inc., Austin Tex.) in 10 mL of trypitcase soy broth (TSB) (Difco, Ann Arbor, Mich.) in a 15 mL sterile loosely tightened screw capped conical tube overnight at 37° C. The tube was held stationary. Upon observation of turbidity, the bacterial suspension was checked for purity by isolation plate and Gram stain. Once determined that the isolate was Proteus mirabilis, a colony from the isolation plate was transferred to 10 mL of TSB in a 15 mL sterile screw capped conical tube and incubated overnight at 37° C. under facultative conditions. Bacterial suspension from this overnight TSB culture was used to inoculate a filter sterilized (0.22 micrometer) solution of 9:1 urine:TSB and incubated for 24 hours at 37° C.

In this Example, three different samples were prepared for analysis. The first sample was prepared by first preparing a urine culture made by blending 9 parts of pooled human urine and 1 part of TSB. The pH of this solution was then measured. This urine mixture was filter sterilized (0.22 micrometer) and was inoculated with 10 microliters of a $10^9$ CFU/mL Proteus mirabilis as prepared above. The urine culture containing the Proteus mirabilis was then incubated at 37° C. overnight to grow the bacteria under facultative conditions. The second sample was prepared identically to the first sample with the exception that, prior to the addition of the Proteus mirabilis, glycine betaine was added to the urine culture to a concentration of 1 milligram/milliliter of urine:TSB. The third sample was prepared identically to the second sample with the exception that glycine betaine was added to a concentration of 2 milligrams/milliliter of urine:TSB.

Upon completion of the incubation periods for each sample, optical density measurements of 200 microliters of each sample were taken. The optical density measurement of each sample was done at 650 nanometers, and from this reading the CFU/mL was calculated.

After optical density measurements were complete, the ammonia production of each sample was measured using an ammonia combination probe (Beckman, Fullerton, Calif.) by record mV using an Orion pH meter (Orion, Boston, Mass.). Orion ammonia standards were used to calibrate the instrument. The results are shown in Table 1.

TABLE 1

| Glycine Betaine (mg/ml) | Bacterial Yield (CFU/mLE+9) | Ammonia Production (ppm) | Ammonia/Cell (ppm/CFUE+8) | pH (no bacteria) |
|---|---|---|---|---|
| 0 | 1.03 | 1538 | 149.2 | 6.19 |
| 1 | 0.83 | 670 | 80.5 | 6.19 |
| 2 | 1.22 | 267 | 21.8 | 6.21 |

As the data in Table 1 indicates, as the concentration of glycine betaine increases in the samples, the production of ammonia by the bacteria decreases. Also, the data indicates that the addition of the glycine betaine did not affect the bacterial yield, which indicates that the growth of the Proteus mirabilis was not inhibited by the glycine betaine, but the metabolism was affected causing a decrease in the amount of ammonia produced per cell. Further, the data indicates that pH did not change in the samples with increasing concentration of glycine betaine. The pH of the sample without bacteria was around 6. The pKa of the carboxylic acid group in glycine is about 4.0; with the starting pH greater than 4.0, this indicates that glycine betaine does not neutralize the ammonia produced by the bacteria, but actually inhibits the production of the ammonia by Proteus mirabilis.

In view of the above, it will be seen that the several objects of the invention are achieved. As various changes could be made in the above-described osmoregulation protector-comprising products without departing from the scope of the invention, it is intended that all matter contained in the above description be interpreted as illustrative and not in a limiting sense.

What is claimed is:

1. An absorbent product for minimizing the amount of ammonia produced by bacteria, said product comprising an osmoregulation protector, selected from the group consisting of glycine betaine, proline betaine, trigonelline, carnitine, and arsenobetaine, said osmoregulation protector being present in an amount capable of interacting with bacteria such that the production of ammonia by the bacteria is minimized.

2. The absorbent product as set forth in claim 1 wherein the osmoregulation protector is capable of interacting with bacteria contained in voided urine.

3. The absorbent product as set forth in claim 1 wherein the product is selected from the group consisting of diapers, training pants, adult incontinence garments, feminine napkins, tampons, interlabial pads, facial tissue, wound management products, bath tissue, diaper pails, liners for diaper pails, refuse containers, paper towels, bed pads, wet wipes, and puppy pads.

4. The absorbent product as set forth in claim 1 wherein the product contains from about 0.001 milligrams/gram of product to about 2 milligrams/gram of product of the osmoregulation protector.

5. The absorbent product as set forth in claim 1 wherein the product contains from about 0.01 milligrams/gram of product to about 2 milligrams/gram of product of the osmoregulation protector.

6. The absorbent product as set forth in claim 1 wherein the product contains from about 0.1 milligrams/gram of product to about 2 milligrams/gram of product of the osmoregulation protector.

7. The absorbent product as set forth in claim 1 wherein the osmoregulation protector is glycine betaine.

8. The absorbent product as set forth in claim 1 wherein the osmoregulation protector is encapsulated into a shell material.

9. The absorbent product as set forth in claim 1 wherein the osmoregulation protector is introduced onto the absorbent product utilizing a process selected from the group consisting of spray coating, slot coating, printing and particle impingement.

10. The absorbent product as set forth in claim 1 wherein the osmoregulation protector is introduced into the absorbent product in combination with a liposome carrier.

11. The absorbent product as set forth in claim 1 wherein the osmoregulation protector is introduced into the absorbent product in combination with an emulsion.

12. An adult incontinence garment for minimizing the amount of ammonia produced by bacteria contained in urine voided by a wearer, said adult incontinence garment comprising an osmoregulation protector, selected from the group consisting of glycine betaine, proline betaine, trigonelline, carnitine, and arsenobetaine, said osmoregulation protector being present in an amount capable of interacting with the bacteria contained in the urine such that the production of ammonia by the bacteria is minimized.

13. The adult incontinence garment as set forth in claim 12 wherein the garment contains from about 0.001 milligrams/gram of product to about 2 milligrams/gram of product of the osmoregulation protector.

14. The adult incontinence garment as set forth in claim 12 wherein the garment contains from about 0.01 milligrams/gram of product to about 2 milligrams/gram of product of the osmoregulation protector.

15. The adult incontinence garment as set forth in claim 12 wherein the garment contains from about 0.1 milligrams/gram of product to about 2 milligrams/gram of product of the osmoregulation protector.

16. The adult incontinence garment as set forth in claim 12 wherein the osmoregulation protector is glycine betaine.

17. A wet wipe for minimizing the amount of ammonia produced by bacteria, said wet wipe comprising a liquid solution and a basesheet, said liquid solution comprising an osmoregulation protector selected from the group consisting of glycine betaine, proline betaine, trigonelline, carnitine, and arsenobetaine, said osmoregulation protector being present in an amount capable of interacting with bacteria on or near the skin's surface such that the production of ammonia by the bacteria is minimized.

18. The wet wipe as set forth in claim 17 wherein the solution contains from about 0.01 milligrams/milliliter of solution to about 2 milligrams/milliliter of solution of the osmoregulation protector.

19. The wet wipe as set forth in claim 17 wherein the solution contains from about 0.1 milligrams/milliliter of solution to about 1 milligram/milliliter of solution of the osmoregulation protector.

20. The wet wipe as set forth in claim 17 wherein the osmoregulation protector is glycine betaine.

21. An adult incontinence garment for minimizing the amount of ammonia produced by bacteria contained in urine voided by a wearer, said garment comprising from about 0.001 milligrams/gram of garment to about 2 milligrams/gram of garment of glycine betaine, said glycine being capable of interacting with the bacteria contained in the urine such that the production of ammonia by the bacteria is minimized.

22. A process for minimizing the amount of ammonia produced by bacteria in voided urine, the process comprising:
    contacting the voided urine with an amount of osmoregulation protector sufficient to interact with the bacteria in the voided urine such that the production of ammonia by the bacteria is minimized, the osmoregulation protector selected from the group consisting of glycine betaine, proline betaine, trigonelline, carnitine, and arsenobetaine.

23. The process as set forth in claim 22 herein the osmoregulation protector is glycine betaine.

24. A process for minimizing the amount of ammonia produced by bacteria in voided urine, the process comprising:
    introducing an osmoregulation protector selected from the group consisting of glycine betaine, proline betaine, trigonelline, carnitine, and arsenobetaine into an absorbent product to be worn by a wearer next to the skin to absorb the voided urine, the osmoregulation protector being present in the absorbent product in an amount sufficient to interact with bacteria in the voided urine such that the production of ammonia by the bacteria is minimized; and
    contacting the absorbent product and osmoregulation protector with urine voided by the wearer such that the osmoregulation protector can interact with bacteria in the urine and decrease the amount of ammonia produced by the bacteria.

25. The process as set forth in claim 24 wherein the absorbent product is selected from a diaper and an incontinence garment.

26. The process as set forth in claim 24 wherein the absorbent product contains from about 0.001 milligrams/gram of product to about 2 milligrams/gram of product of the osmoregulation protector.

27. The process as set forth in claim 24 wherein the absorbent product contains from about 0.01 milligrams/gram of product to about 2 milligrams/gram of product of the osmoregulation protector.

28. The process as set forth in claim 24 wherein the osmoregulation protector is glycine betaine.

* * * * *